United States Patent [19]
Leschinsky

[11] Patent Number: 5,928,132
[45] Date of Patent: Jul. 27, 1999

[54] CLOSED CHEST INTRA-AORTIC BALLOON BASED VENTRICULAR ASSIST DEVICE

[75] Inventor: Boris Leschinsky, Waldwick, N.J.

[73] Assignee: Datascope Investment Corp., Montvale, N.J.

[21] Appl. No.: 09/052,491

[22] Filed: Mar. 31, 1998

[51] Int. Cl.[6] .................................................. A61M 1/12
[52] U.S. Cl. ................................................................ 600/16
[58] Field of Search ....................................... 600/16–18

[56]         References Cited

U.S. PATENT DOCUMENTS

| | | | |
|---|---|---|---|
| 3,974,825 | 8/1976 | Normann | 600/17 |
| 4,014,317 | 3/1977 | Bruno | 600/18 |
| 4,861,330 | 8/1989 | Voss | 600/18 |
| 4,906,229 | 3/1990 | Wampler | 600/16 |
| 5,092,844 | 3/1992 | Schwartz et al. | 604/151 |
| 5,169,378 | 12/1992 | Figuera | 600/16 |
| 5,332,403 | 7/1994 | Kolfe | 600/16 |
| 5,820,542 | 10/1998 | Dobak | 600/16 |

FOREIGN PATENT DOCUMENTS

| | | | |
|---|---|---|---|
| WO 96/32971 | 10/1996 | WIPO | A61M 1/10 |
| WO 97/02850 | 1/1997 | WIPO | A61M 1/10 |

OTHER PUBLICATIONS

Imanishi K. et al, A Percutaneously Accessible Pulsatile Left Ventricular Assist Device: Modified Assist Device Type 5, Artificial Organs, 20(2):147–151 (1996).

Verkerke B. et. al, The PUCA Pump: A Left Ventricular Assist Device, Artificial Organs, 17(5):365–368 (1993).

*Primary Examiner*—William E. Kamm
*Attorney, Agent, or Firm*—Abraham P. Ronai

[57]         ABSTRACT

A closed chest intra-aortic balloon catheter based ventricular assist device comprising an intra-aortic balloon (IAB) catheter and a pumping chamber having a smaller diameter portion and a more proximal larger diameter portion. The IAB catheter balloon membrane is disposed within the larger diameter portion. The entire device is inserted percutaneously into the aorta of a patient such that the tip of the IAB catheter is just distal to the left subclavian artery and the distal end of the smaller diameter portion is in the left ventricle. The smaller diameter portion has an intake valve at its distal end which acts as a one-way valve allowing blood to flow into the lumen of the pumping chamber but not out of it. The pumping chamber has one or more outlet valves. As the balloon membrane deflates, pressure in the pumping chamber drops below that in the left ventricle, and as a result, blood flows into the pumping chamber. As the balloon membrane inflates, increased pressure in the pumping chamber forces the intake valve shut and forces blood through the outlet valves into the aorta. The pumping chamber becomes substantially rigid after insertion so as to withstand arterial blood pressure.

17 Claims, 11 Drawing Sheets

CLOSED CHEST INTRA-AORTIC BALLOON BASED VENTRICULAR ASSIST DEVICE

BACKGROUND OF THE INVENTION

1. Field of the Invention

The present invention relates generally to devices and systems for augmenting cardiac output, and specifically to intra-aortic cardiac assist pumps.

2. Description of the Prior Art

Intra-aortic and intra-ventricular cardiac assist devices are well known in the art. These devices are generally used to reduce the heart's work load after insult or surgery. They may also be used to increase blood flow from the left ventricle of the heart into the aorta in cases of insufficient cardiac output due, for example, to acute or chronic heart ailments or to interference with normal cardiac function during surgery.

Cardiac assist devices fall into two basic categories, those comprising an external pumping chamber which remains outside the body during the entire course of the therapy (extracorporeal) and those comprising an internal pumping chamber which remains inside of the body (intracorporeal). One major drawback to an internal pumping chamber is that it requires extensive surgery for implantation and removal of the device.

Devices with external pumping chambers also have a number of drawbacks. U.S. Pat. No. 4,014,317, which is incorporated herein by reference, describes a cardiocirculatory assist cannula with a an external balloon pump and cardiac pacing electrode. The cannula is inserted percutaneously through the aorta so that its distal end is inside the left ventricle of the heart. During systole, inlet valves on the cannula inside the left ventricle remain open, and the contraction of the ventricle forces blood to flow into the cannula. Then, during diastole, the blood flows out, into the aorta, through one or more outlet valves along the cannula downstream from the inlet valve. A gas-filled chamber, similar in function to an Intra-Aortic Balloon Pump (IABP), is connected to the cannula external to the patient and downstream of the outlet valves. The balloon is typically inflated during diastole and deflated during systole, to assist in perfusion of the coronary arteries. The cannula has a long and narrow shape which presents a significant blood flow restriction, and thus, limits the effective stroke volume of the device. Accordingly, the device is of limited usefulness in augmenting the blood output of a weakened or failing heart.

U.S. Pat. No. 4,906,229, which is also incorporated herein by reference, describes a high-frequency transvalvular axisymmetric external blood pump. The pump includes a small internal volume in a stiff barrel, which may be alternately expanded and reduced by pneumatic or hydraulic pressure which is exerted via a flexible membrane radially surrounding the volume. The volume has intake and outlet ends, with one-way axial valves at both of the ends, so that blood can flow only from the heart into the aorta. The pump is connected via the one-way intake valve to a cannula, which is inserted into the left ventricle of the heart through the aortic valve. When the internal volume is expanded, blood flows into the pump from the ventricle. The volume is then reduced, and the blood is ejected into the aorta through the outlet end. This pump is designed to operate at a frequency of 600 to 1,000 cycles per minute. Since the stroke volume of the pump is typically only about 3–5 cc, these high cycle rates are needed in order to provide adequate perfusion.

A major drawback of the prior art extracorporeal intra-aortic cardiac assist devices involves an inherent design limitation of said devices. The prior art extra-corporeal intra-aortic cardiac assist devices pump blood out of the left ventricle, through a cannula, and into a downstream portion of the artery. There is a desire to make the inner diameter of the cannula as large as possible so as to allow for the greatest possible blood flow rate through said cannula. There is also a desire, however, to make the outer diameter of the cannula as small as possible to ease its insertion into the artery and so as not to substantially reduce the blood flow in the artery around the cannula. As a result of these competing design goals cannulae are generally designed large enough to accommodate only 20–40 cc of blood per heart cycle. The average patient, however, requires approximately 80–100 cc of blood per heart cycle for full blood flow support.

Aside from the internal/external pumping chamber distinction, cardiac assist devices are also categorized according to their pump drives, which are either continuous or pulsatile flow. In the Hemopump Cardiac Assist System, distributed by Johnson & Johnson Interventional Systems, a cannula containing a special, miniature rotor pump mechanism is inserted into the aorta. The pump is driven by a drive unit outside the body, to pump blood continuously from the aorta into the rest of the arterial system, thereby supplementing to some degree the heart's natural output rate. A system of this type is similarly described in U.S. Pat. No. 5,092,844, which is incorporated herein by reference. A drawback of this system is that the outer diameter of the pump, and accordingly the pump's output, is limited due to the need for insertion through the femoral artery. A further drawback of this system, and of continuous-flow devices in general, concerns the belief that pulsatile pumps provide more effective long-term support than continuous-flow devices since they approximate more closely the natural pump action of the heart.

One of the best-known and most widely-used intra-aortic pump systems is the Intra-Aortic Balloon Pump (IABP), comprising a catheter, having an inflatable balloon at its distal end, which is inserted through an artery into the aorta. The balloon is alternately inflated and deflated by an external pump drive, so as to alternately increase and decrease blood pressure in the aorta, in counter phase with the beating of the heart, in order to assist the left ventricle in propelling blood into the arterial system. The Intra-Aortic Balloon (IAB) catheter is a popular cardiac assist device because it can be inserted percutaneously, and therefore, avoids the major surgery associated with implantation and removal of an internal ventricular assist device. The IABP, however, provides only limited augmentation of the heart's natural, unassisted output, and is not adequate for overcoming a major heart failure.

While these devices may be suitable for the particular purpose employed, or for general use, they would not be as suitable for the purposes of the present invention as disclosed hereafter.

SUMMARY OF THE INVENTION

Accordingly, it is an object of the invention to produce a cardiac assist device which is capable of overcoming heart failure by providing full blood flow support.

It is another object of the invention to produce a cardiac assist device which can be inserted percutaneously or through a limited cut-down procedure, and therefore, does not require extensive thoracic surgery for implantation and removal.

It is a further object of the invention to produce a cardiac assist device which produces a pulsatile blood flow which more closely approximates the natural pump action of the heart.

It is a still further object of the invention to produce a cardiac assist device which does not substantially reduce blood flow in the occupied artery.

The invention is a closed chest intra-aortic balloon catheter based ventricular assist device comprising an intra-aortic balloon (IAB) catheter and a pumping chamber having a smaller diameter portion and a more proximal larger diameter portion. The IAB catheter balloon membrane is disposed within the larger diameter portion. The entire device is inserted percutaneously into the aorta of a patient such that the tip of the IAB catheter is just distal to the left subclavian artery and the distal end of the smaller diameter portion is in the left ventricle. The smaller diameter portion has an intake valve at its distal end which acts as a one-way valve allowing blood to flow into the lumen of the pumping chamber but not out of it. The pumping chamber has one or more outlet valves. As the balloon membrane deflates, pressure in the pumping chamber drops below that in the left ventricle, and as a result, blood flows into the pumping chamber. As the balloon membrane inflates, increased pressure in the pumping chamber forces the intake valve shut and forces blood through the outlet valves into the aorta. The pumping chamber becomes substantially rigid after insertion so as to withstand arterial blood pressure.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
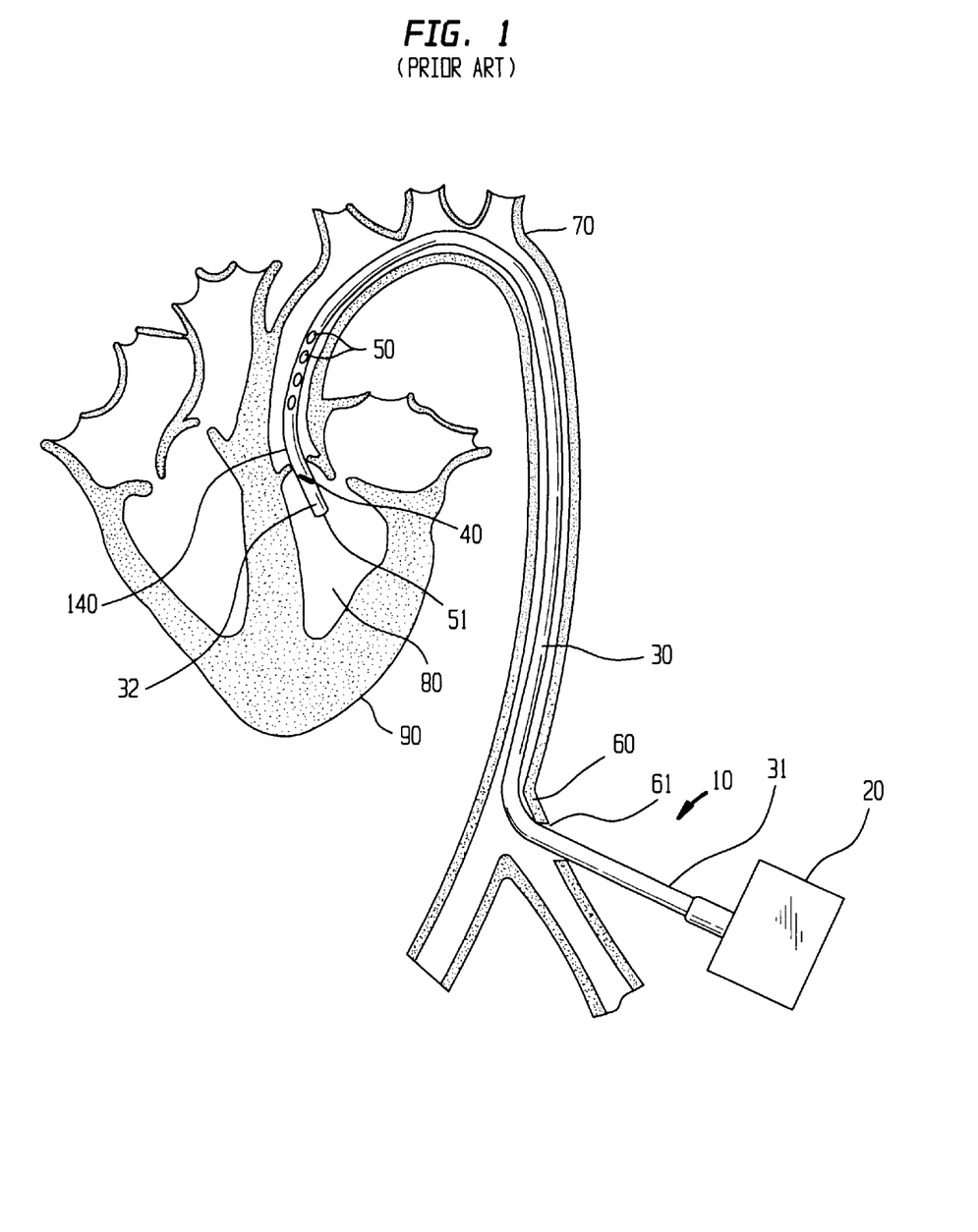
FIG. 1 is a longitudinal cross section of a prior art cardiac assist pump system inserted into the aorta of a patient.

FIG. 1 illustrates a longitudinal cross section of an inserted prior art cardiac assist pump, generally designated 10, comprising an external pump 20 and a cannula 30 having a proximal end 31, a distal end 32, an intake valve 40, outlet valves 50, and a lumen 51. Preferably the cannula 30 is inserted percutaneously, through an incision 61 in the peripheral artery 60, or another suitable artery such as the femoral artery, and passed upstream through aorta 70 and aortic valve 140 into the left ventricle 80 of heart 90. The method of insertion is substantially similar to methods for insertion of other types of cardiac cannulae known in the art. The length of the cannula 30 is approximately 60 cm, which is generally sufficient to ensure that when the distal end of the cannula 30 is positioned in the left ventricle 80 the proximal end of the cannula 30 remains outside the body of the patient, adjacent to the incision 61. Alternatively, the cannula 30 may be inserted surgically through a suitable incision elsewhere in the arterial system.

Once the cannula 30 is in place the pump 20 creates a pressure differential in the cannula 30, and as a result, the intake valve 40, located at the distal end 32 of the cannula 30, is opened, and blood flows from the left ventricle 80 into lumen 51. Outlet valves 50 are kept closed while the blood fills the lumen 51. After an outside chamber (not shown) fills up with blood, the pump 20 creates an opposite pressure differential in the chamber, and as a result, the intake valve 40 is closed and the outlet valves 50 are opened and the blood is forced out of the lumen 51 and into the aorta 70.

Figure 2:
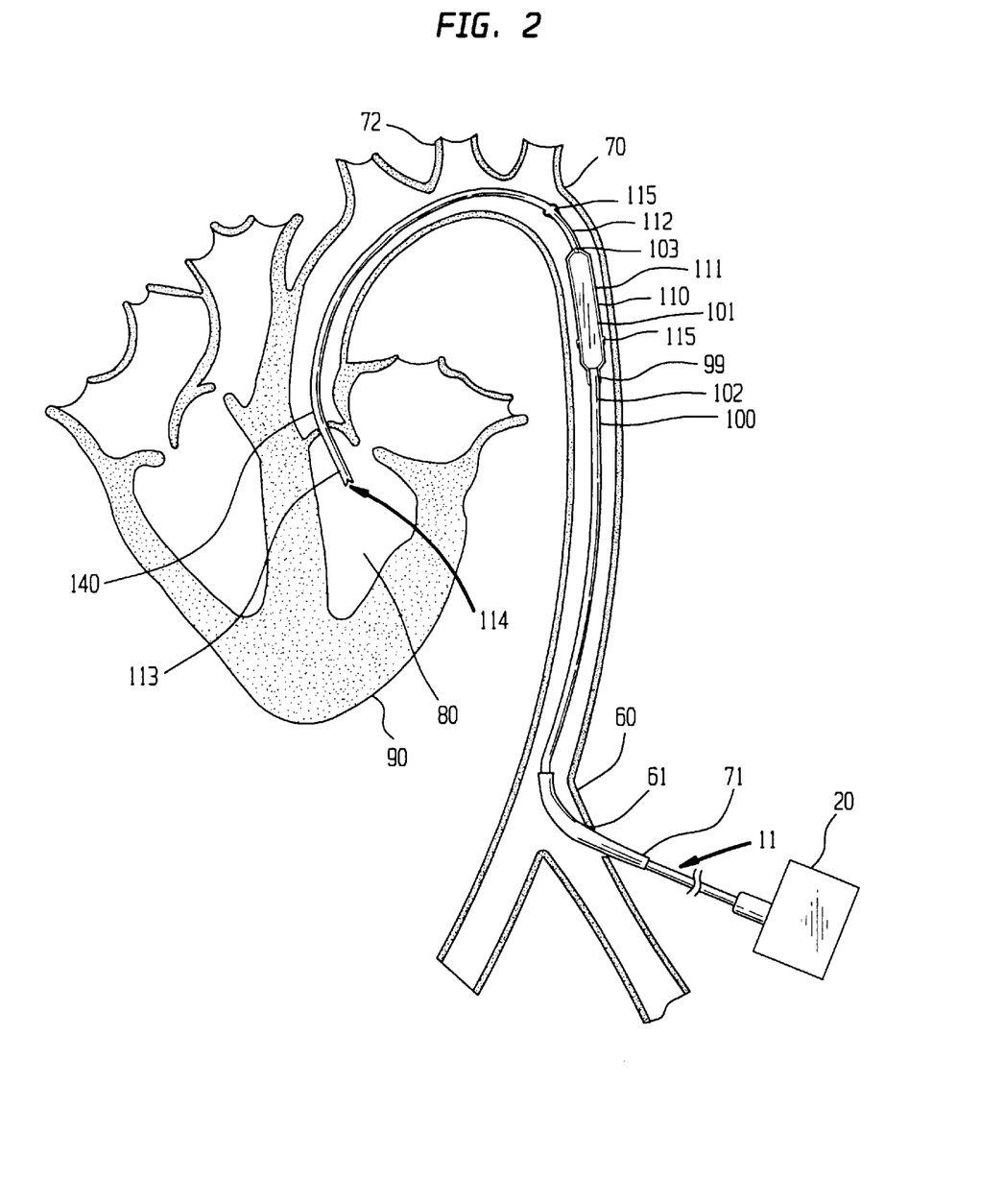
FIG. 2 is longitudinal cross section of the present invention, a closed chest IAB-based ventricular assist device, inserted into the aorta and left ventricle of a patient.

FIG. 2 illustrates a longitudinal cross section of the present invention, generally designated 11, inserted into the aorta 70 of a patient. The present invention 11 comprises an Intra-Aortic Balloon (IAB) catheter 100 and a pumping chamber 110 having outlet valves 115. The pumping chamber 110 comprises a larger tube chamber portion 111, having a proximal end 99, and a smaller tube cannula portion 112, having a distal end 113. Note that the directional term "distal" refers to a location closer to the heart. A leaflet intake valve 114, or other suitable intake valve, is attached to the distal end 113 of the smaller tube cannula portion 112 of the pumping chamber 110. The IAB catheter 100 comprises generally a balloon membrane 101, an outer tube 102, a tip 103, and an external pump 20. The IAB catheter 100 is generally inserted percutaneously into the aorta 70 through an optional insertion sheath 71, and the tip 103 is placed just distal to the left subclavian artery 72. Identical to prior art IABs the external pump 20 shuttles a non-blood material, such as gas, back and forth in the outer tube 102 causing the balloon membrane 101 to inflate and deflate rapidly. The balloon membrane 101 is slidingly disposed within the larger tube chamber portion 111 of the pumping chamber 110. The proximal end 99 of the larger tube chamber portion 111 is slidingly attached to the outer tube 102 of the IAB catheter 100 such that blood cannot escape through said proximal end 99.

Figure 3:
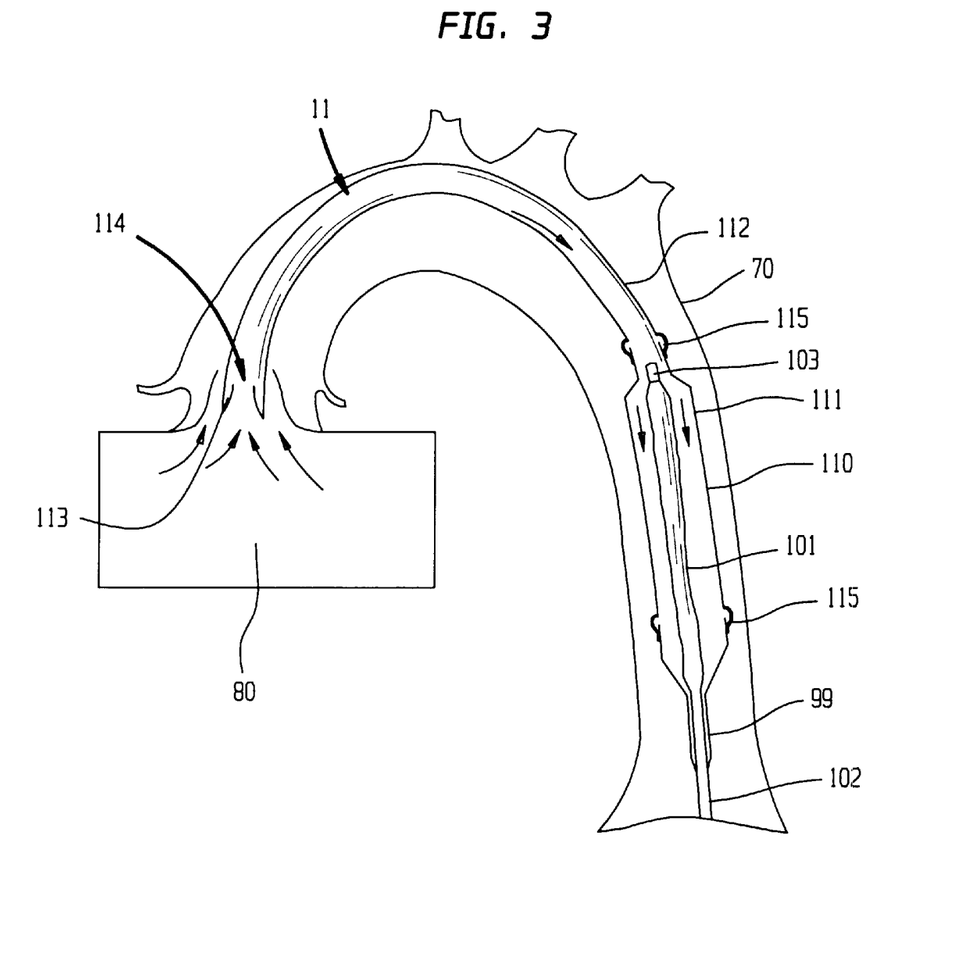
FIG. 3 is a longitudinal cross section of a distal portion of the inserted closed chest IAB-based ventricular assist device, illustrated in FIG. 2, with the balloon membrane in a deflated state.
Figure 4:
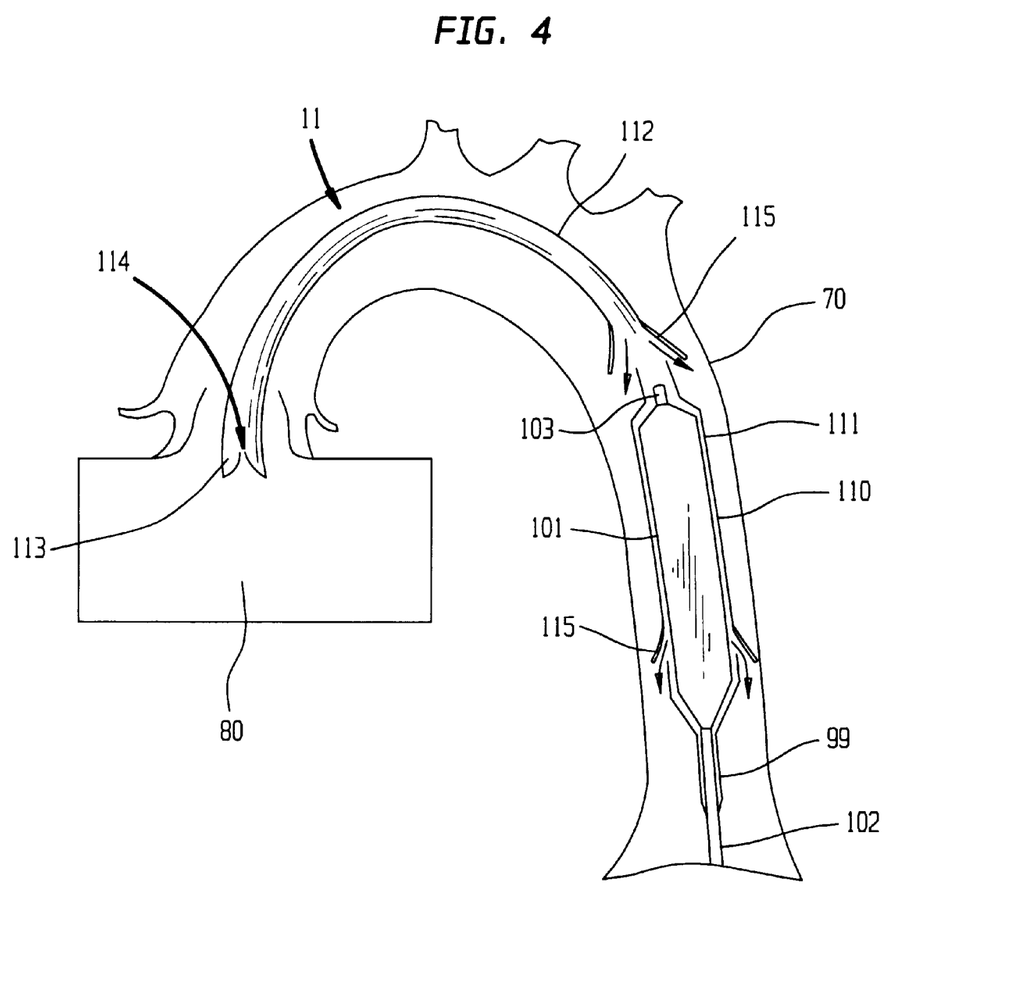
FIG. 4 is a longitudinal cross section of a distal portion of the inserted closed chest IAB-based ventricular assist device, illustrated in FIG. 2, with the balloon membrane in an inflated state.

FIGS. 3 and 4 illustrate a longitudinal cross section of the pumping chamber 110 and a distal portion of the IAB catheter 100 inserted into the aorta 70 of a patient. FIG. 3 illustrates the means by which blood is forced into the smaller tube cannula portion 112. The balloon membrane 101 is in a deflated state, and as a result, the pressure in the pumping chamber 110 is lower than the pressure in the aorta 70, and preferably, is close to that in the left ventricle 80. The pressure differential causes the leaflet intake valve 114 to open and allow blood to flow into the distal end 113 of the smaller tube cannula portion 112. Lower pressure in the pumping chamber 110 also causes the outlet valves 115 to close, thereby, preventing any blood from escaping through said outlet valves 115 into the aorta 70. Note that as illustrated in FIG. 3 the aortic valve 140 opens in concert with the outlet valves 115. This representation assumes that the heart 90 is pumping synchronously with the closed chest IAB-based ventricular assist device 11. However, use of the present invention 11 is anticipated with a totally failed left heart. In such a case, the diameter of the smaller tube cannula portion 112 may be made larger so as to accommodate the entire blood flow. Note further that the smaller tube cannula portion 112 and the annular area between the balloon membrane 101 and the larger tube chamber portion 111 are the only blood containing portions of the present invention 11. The IAB catheter 100 may be considered the non-blood containing portion of the present invention 11. FIG. 4 illustrates the means by which the blood is forced out of the pumping chamber 110. The balloon membrane 101 is inflated causing the pressure in the pumping chamber 110 to increase. As a result, the intake valve 114 is forced shut by blood attempting to reenter the left ventricle 80, and the outlet valves 115 are forced open allowing blood in both the smaller tube cannula portion 112 and the larger tube chamber portion 111 to flow into the aorta 70. Note that outlet valves 115 may be located throughout the pumping chamber 110. Note that the present invention 11, with minor variations, is anticipated for use as a right ventricular assist device as well.

Figure 5:
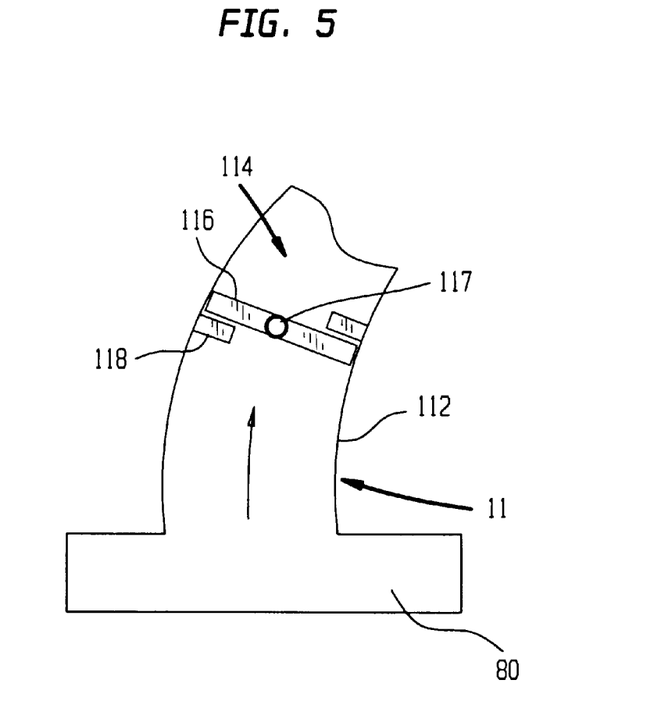
FIG. 5 is a longitudinal cross section of a distal end of a closed chest IAB-based ventricular assist device with an alternate embodiment of the intake valve in a transverse closed state.
Figure 6:
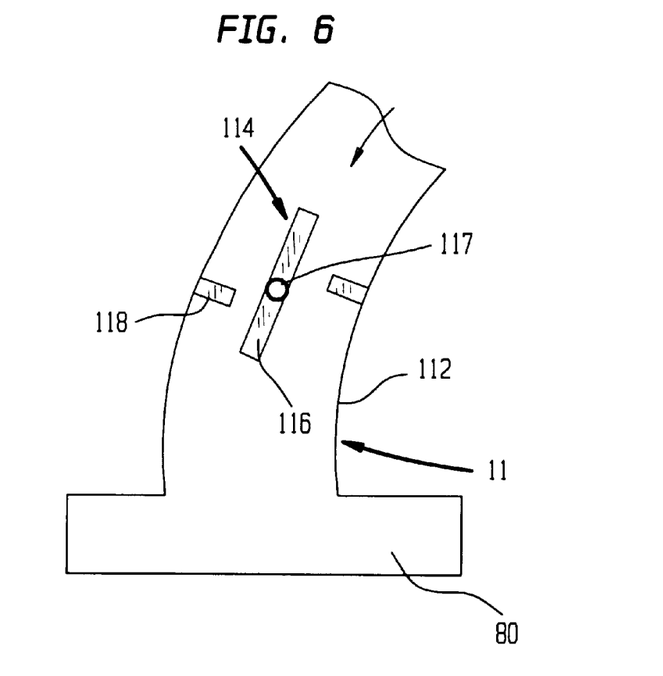
FIG. 6 is a longitudinal cross section of a distal end of a closed chest IAB-based ventricular assist device with an alternate embodiment of the intake valve in a longitudinal open state.

FIG. 5 illustrates an alternate embodiment of the intake valve 114. The intake valve 114 comprises a disk 116 that is rotatably attached to the smaller tube cannula portion 112 by means of a pin 117. As blood attempts to flow into the left ventricle 80 the disk 116 rotates to its transverse closed position and stays there as a result of stoppers 118, preventing blood from reentering the left ventricle 80. As blood attempts to flow out from the left ventricle 80, as illustrated by FIG. 6, the disk 116 spins back to its longitudinal open position and allows the blood to flow into the pumping chamber 110. Note that different forms of intake and outlet valves are anticipated.

Figure 7:
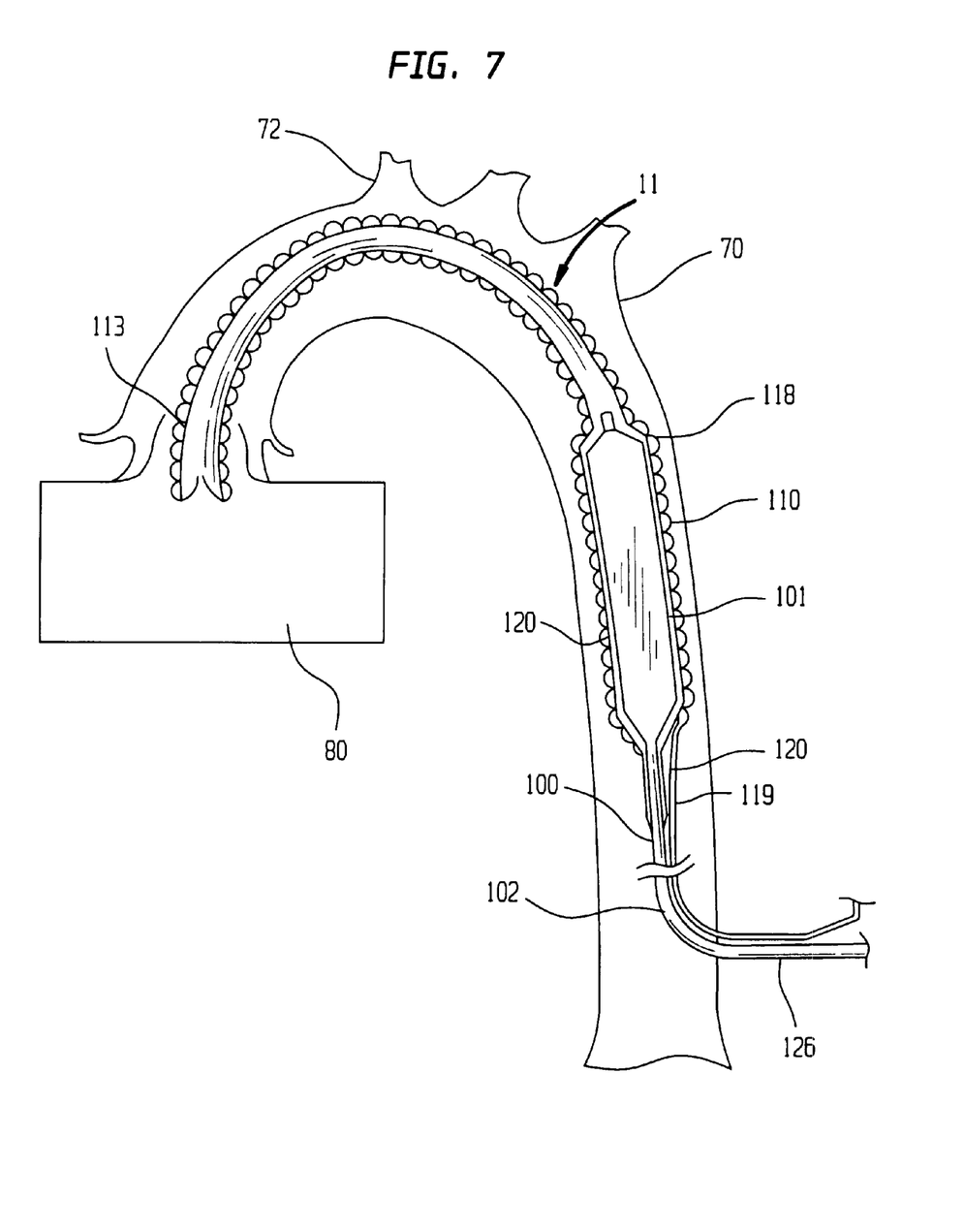
FIG. 7 is a longitudinal cross section of a fluid-filled pumping chamber disposed about an IAB catheter balloon membrane and inserted into the aorta and left ventricle of a patient.
Figure 8:
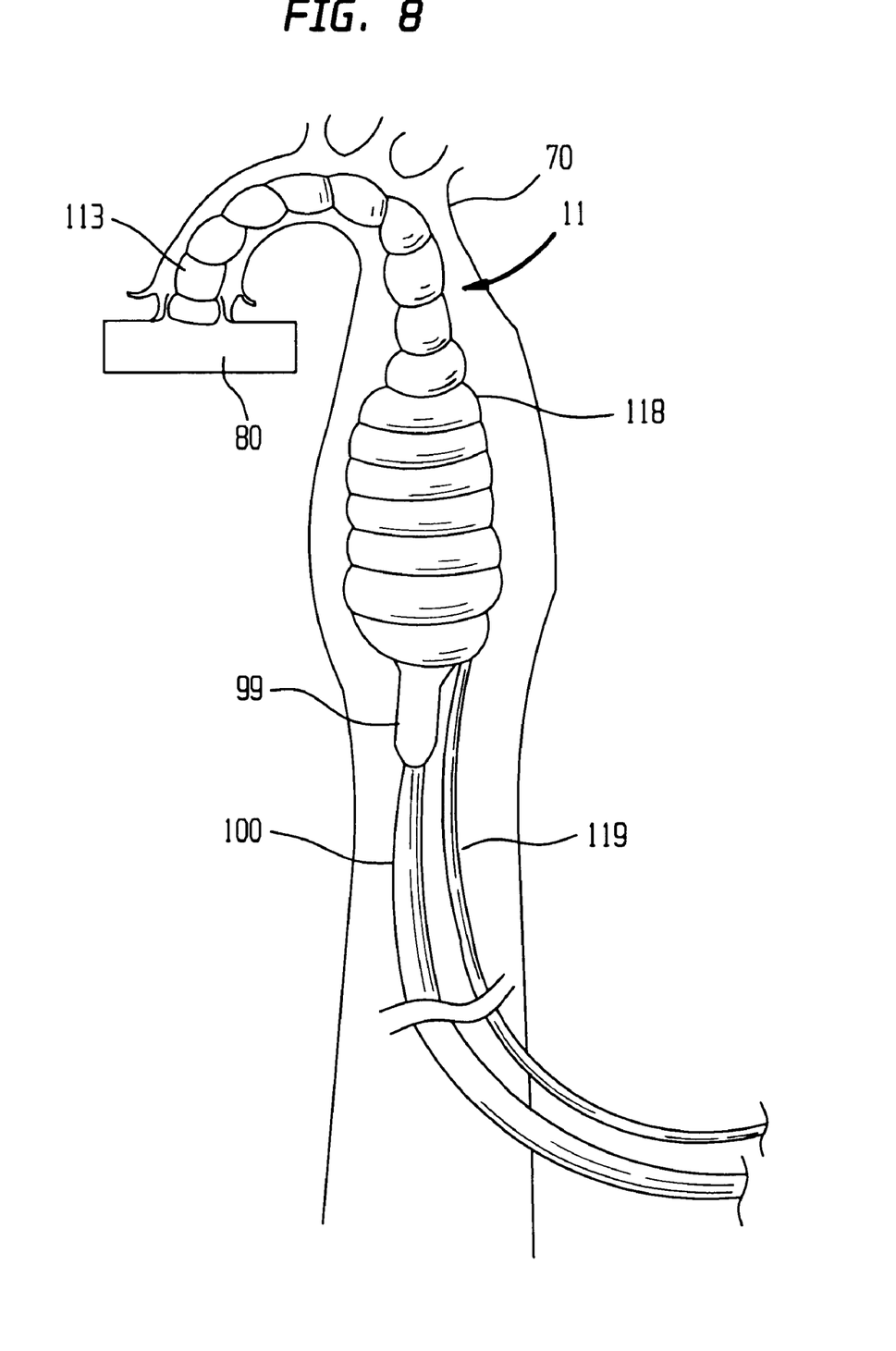
FIG. 8 illustrates a perspective view of the fluid-filled pumping chamber illustrated in FIG. 7.

Preferably the IAB catheter 100 and the pumping chamber 110 are inserted percutaneously in series or as one unit. The method for inserting an IAB catheter is well known in the art. The preferred embodiment of the pumping chamber 110, capable of being inserted percutaneously, is illustrated in FIGS. 7–8. The pumping chamber 110 must be able to withstand the high pressures generated in the aorta 70, as a result of the deflation of the balloon membrane 101, during actual blood pumping, and yet it must also be flexible enough during insertion to be capable of being advanced into the aorta 70. FIG. 7 illustrates a longitudinal cross section of the fluid-filled pumping chamber 110, disposed about the balloon membrane 101 of the IAB catheter 100, which demonstrates these properties. The IAB catheter 100 is percutaneously inserted such that the tip 103 is just proximal the left subclavian artery 72. The pumping chamber 110 has a pump tube 118, having a distal end 113 and a proximal end 99, and a fluid delivery tube 119 attached to the pump tube 118. The pumping chamber 110 is disposed about a proximal end 126 of the IAB catheter 100 and advanced into the aorta 70 such that distal end 113 of the pump tube 118 enters the left ventricle 80. The proximal end 99 of the pump tube 118 is slidingly attached to the outer tube 102 of the IAB catheter 100 such that blood cannot escape through said proximal end 99. A lumen 120 extends the entire length of the fluid delivery tube 119 and runs in a helical or other similar manner around the pump tube 118. Once positioned in the aorta 70 the lumen 120 is filled with fluid. The fluid-filled lumen 120 increases the rigidity of the pumping chamber 110 such that it is capable of withstanding pressures generated in the aorta 70 during deflation of the balloon membrane 101. Upon completion of therapy, the fluid is pumped out of the lumen 120 and the pumping chamber 110 is once again supple and small enough to be removed from the aorta 70 percutaneously. FIG. 8 illustrates a perspective view of the fluid-filled pumping chamber 110 illustrated in FIG. 7. As an alternative to the fluid-filled helical lumen 120, fluid-filled pockets or fluid-filled surface sectors, of various geometries, may be used.

Figure 9:
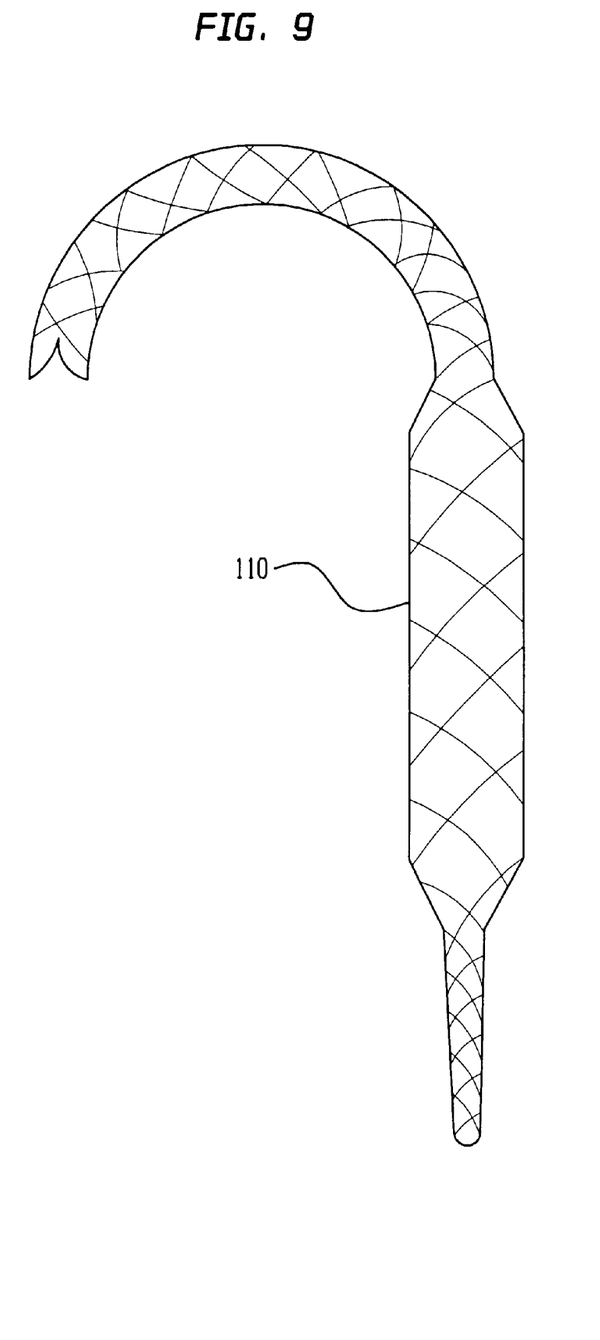
FIG. 9 is a plain view of a third embodiment of the pumping chamber in its unstretched larger diameter state.
Figure 10:
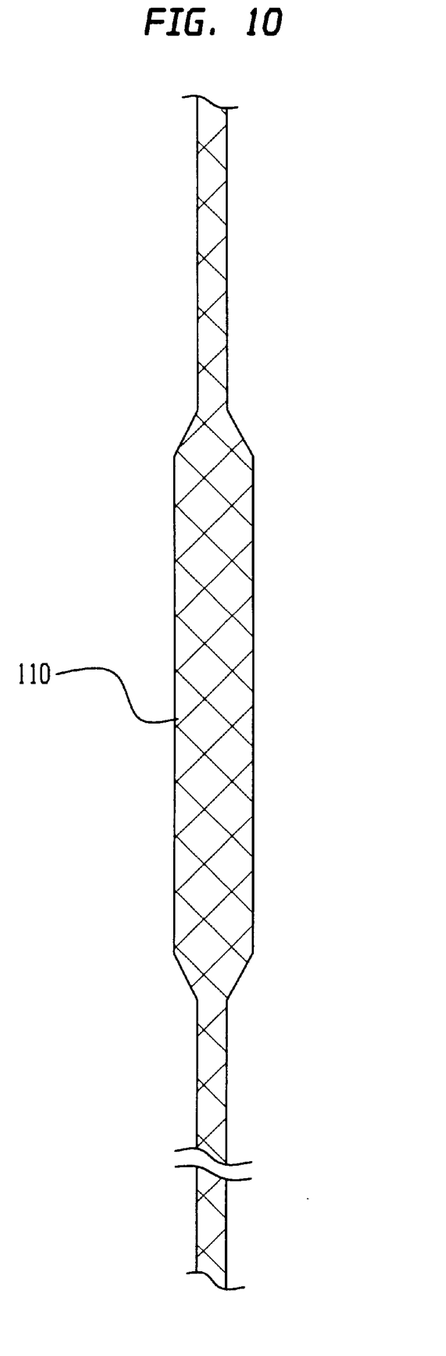
FIG. 10 is a plain view of the third embodiment of the pumping chamber is its stretched smaller diameter state.

FIG. 9 illustrates an alternate pumping chamber 110 made from intercoiled wires covered with an elastic leak proof or other suitable material, similar to expandable stents on the market, and has the property that when pulled or stretched its cross sectional diameter decreases. Insertion of the closed chest IAB-based ventricular assist device 11 incorporating the pumping chamber 110, as illustrated in FIG. 9, comprises the following steps. The IAB catheter 100 is first inserted into the aorta 70. Next, the pumping chamber 110, in a stretched state, is advanced over the IAB catheter 100 into the aorta 70. Upon positioning of the pumping chamber 110, such that the balloon membrane 101 of the IAB catheter 100 is disposed within the pumping chamber 100, the pumping chamber 110 is released and allowed to expand from its smaller diameter stretched state to its larger diameter unstretched state. FIG. 9 illustrates a plain view of the pumping chamber 110 in its unstretched state. FIG. 10 illustrates a plain view of the pumping chamber 110 in its stretched state. The pumping chamber 110 is attached to the IAB catheter 100 in the same manner as the pumping chamber 110 illustrated in FIG. 2. Upon completion of therapy, the pumping chamber 110 is stretched to its smaller diameter stretched state and is then removed percutaneously. After removal of the pumping chamber 110 the IAB catheter 100 is removed percutaneously. The pumping chamber 110 is inserted into and removed from the patient in a manner similar to other expandable stents on the market, such as the Corvita stent (produced by Corvita Corp, Miami, Fla.). As an alternative method of insertion, the IAB catheter 100 may be inserted after insertion of the pumping chamber 110.

Figure 11:
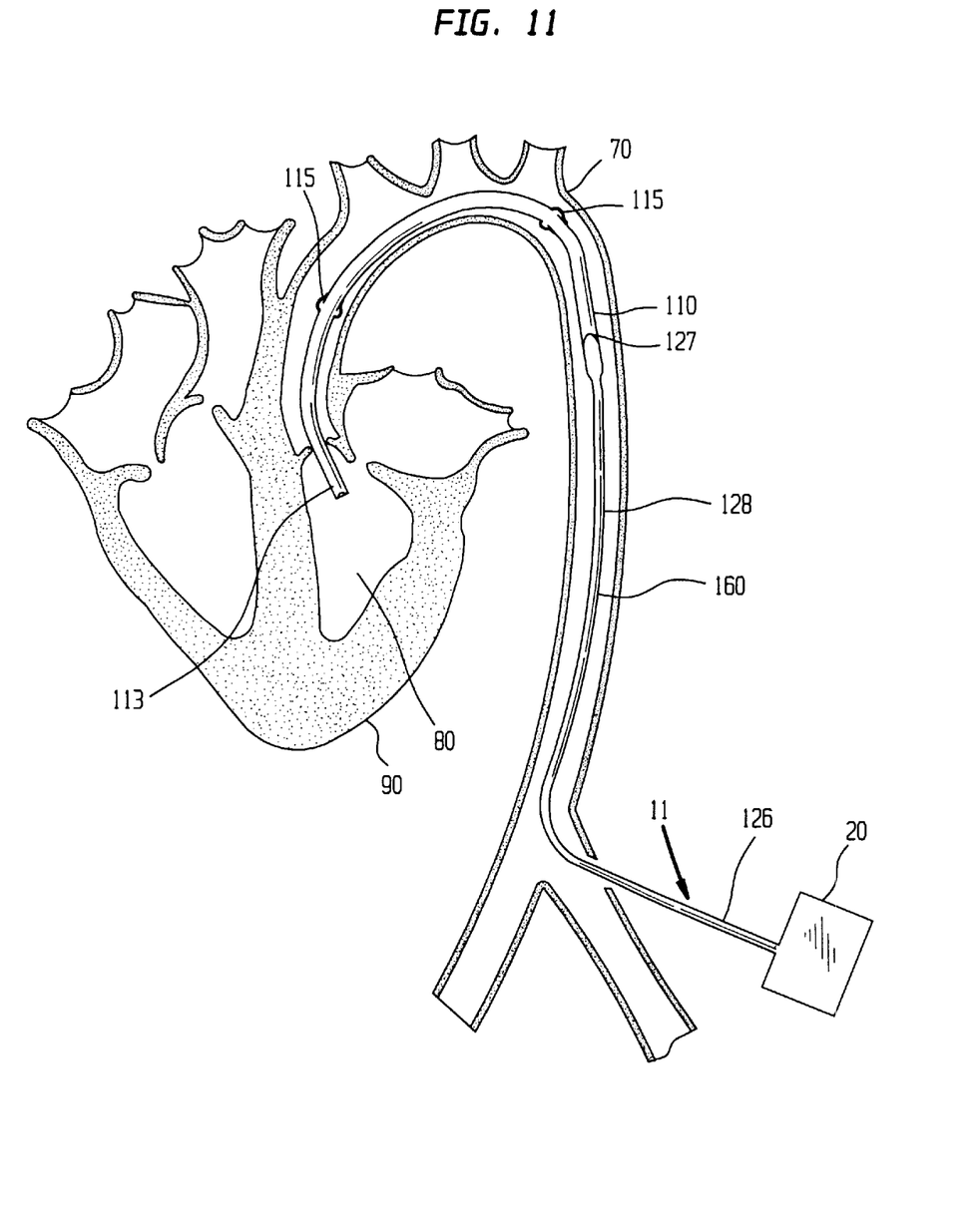
FIG. 11 is longitudinal cross sectional view of an alternate embodiment of the closed chest IAB-based ventricular assist device having a diaphragm.

FIG. 11 illustrates a longitudinal cross section of an alternate embodiment of the present invention 11 inserted into the aorta 70 comprising a cannula 160 having a gas tube portion 128, a proximal end 126, and a pumping chamber 110 having a distal end 113 and a diaphragm 127. The proximal end 126 of the gas tube portion 128 is connected to an external non-blood pump 20. The distal end of the pumping chamber 110 is inserted into the left ventricle 80 of the heart 90. Similar to the first embodiment of the present invention 11, blood flow is limited only to the pumping chamber 110. The pumping chamber 110 is the only blood containing portion of the present invention 11. The gas tube portion 128 is filled with a non-blood material, such as helium. The gas tube portion 128 basically replaces the IAB catheter 100, as illustrated in FIG. 2, as the non-blood containing portion of the present invention 11. The diameter of the gas tube portion 128 may be made smaller than the diameter of the pumping chamber 110. Reduction of the diameter of the gas tube portion 128 allows for more blood flow around the gas tube portion 128 and thus improves circulation in the patient during the procedure.

Figure 12:
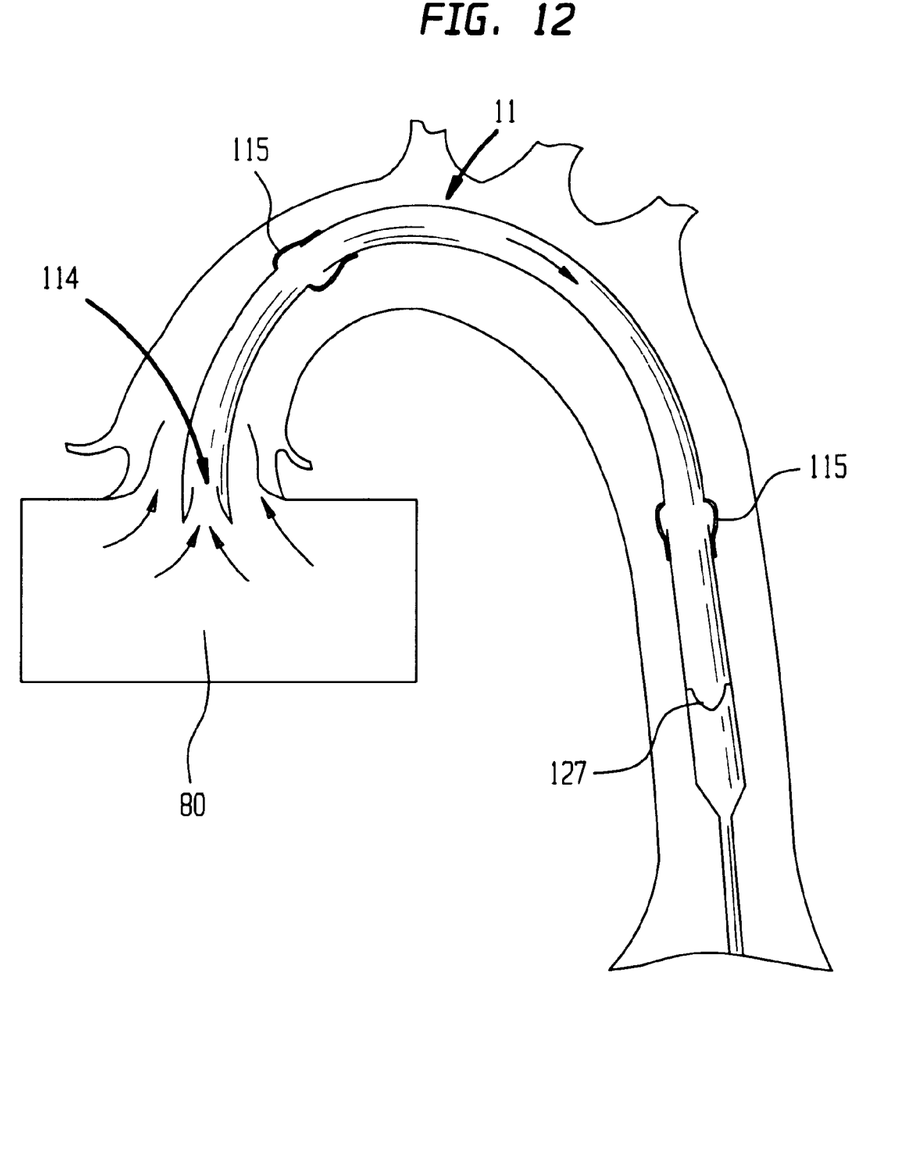
FIG. 12 is a longitudinal cross sectional view of a distal portion of the aorta and the closed chest IAB-based ventricular assist device with a diaphragm in a blood intake position.
Figure 13:
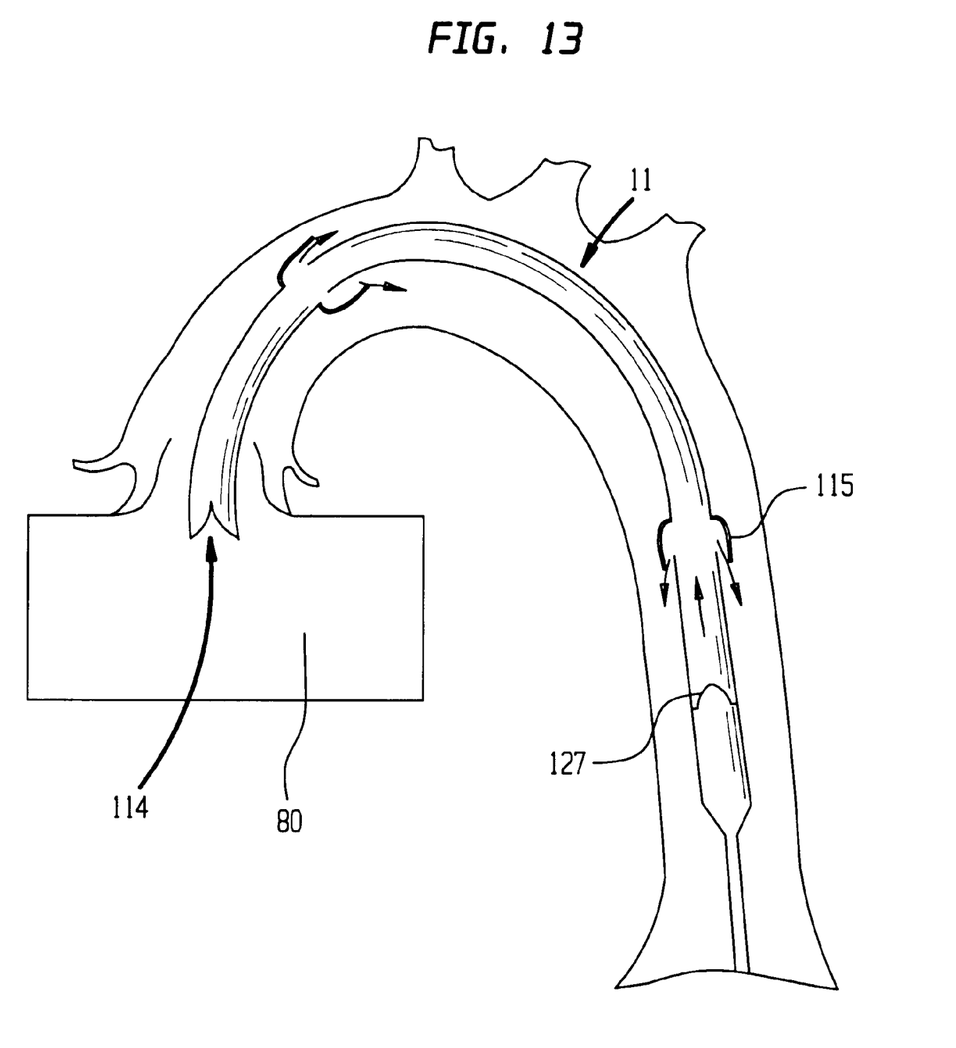
FIG. 13 is a longitudinal cross sectional view of a distal portion of the aorta and the closed chest IAB-based ventricular assist device with a diaphragm in a blood pump position.

As illustrated in FIG. 12, as soon as the pump 20 (FIG. 11) decreases the pressure in the gas tube portion 128 the diaphragm 127 moves to a blood intake position, and as a result, the outlet valves 115 close, the intake valve 114 opens, and blood rushes into the pumping chamber 110. FIG. 12 illustrates a longitudinal cross section of a distal portion of the alternate embodiment illustrated in FIG. 11 with the diaphragm 127 in a blood intake state. As illustrated in FIG. 13, as soon as the pump 20 increases the pressure in the gas tube portion 128 the diaphragm moves to a blood pump position, and as a result, the intake valve 114 closes, the outlet valves 115 open, and blood rushes out of the pumping chamber 110 into the aorta 70.

What is claimed is:

1. A device for pumping blood comprising:
   (a) a blood containing portion comprising a pumping chamber having an outer diameter which defines and encloses a lumen therein, said pumping chamber having a distal end, a proximal end, at least one one-way outlet valve, and at least one one-way intake valve, the pumping chamber is for insertion through a blood vessel of a subject such that the distal end is placed inside a ventricle of the heart of said subject, blood enters the lumen from the ventricle through the intake valve which is adjacent to the distal end of the pumping chamber, blood exits the lumen through the outlet valve which is proximal the intake valv, the blood containing portion is contained entirely within the body of the subject; and
   (b) a non-blood containing portion having an outer diameter and a proximal end connected to a means for changing the volume of blood in the blood containing portion by changing the volume of the non-blood containing portion, when the volume of the non-blood containing portion is decreased the volume of the blood-containing portion correspondingly increases by blood flow from the ventricle through the intake valve and into the lumen, and when the volume of the non-blood containing portion is increased the volume of the blood-containing portion correspondingly decreases by blood flow out of the outlet valve and into the blood vessel of the subject.

2. The device for pumping blood as claimed in claim 1 wherein the outer diameter of the non-blood containing portion is smaller than the outer diameter of the pumping chamber.

3. The device for pumping blood as claimed in claim 1 wherein the means for changing the volume of blood in the blood containing portion comprises a non-blood pump attached to the proximal end of the non-blood containing portion and a flexible diaphragm which separates the blood containing portion and the non-blood containing portion and which moves between a blood intake position and a blood pump position, the non-blood pump increases the volume of the non-blood containing portion by increasing the pressure in the non-blood containing portion and decreases the volume of the non-blood containing portion by decreasing the pressure in the non-blood containing portion, when pressure in the non-blood containing portion is made higher than pressure in the blood containing portion the diaphragm moves to the blood pump position causing blood to flow out of the blood containing portion into the blood vessel via the outlet valves, when pressure in the non-blood containing portion is made lower than pressure in the blood containing portion the diaphragm moves to the blood intake position causing blood to enter the blood containing portion via the intake valve.

4. The device for pumping blood as claimed in claim 1 wherein the means for changing the volume of blood in the blood containing portion comprises a non-blood pump and a balloon membrane which separates the blood containing portion and the non-blood containing portion and which is enveloped within the blood containing portion, the non-blood containing portion contains a non-blood material, the non-blood pump inflates the balloon membrane with the non-blood material and also deflates the balloon membrane, as the balloon membrane is inflated some blood contained within the blood-containing portion is forced out of the blood containing portion via the outlet valve, as the balloon membrane is deflated blood enters the blood containing portion via the intake valve.

5. A device for pumping blood comprising a cannula having a gas tube portion, a pumping chamber, and a diaphragm disposed within said cannula separating the gas tube portion and the pumping chamber which moves between a blood pump position and a blood intake position, the pumping chamber has at least one intake valve adjacent to its distal end and at least one outlet valve further away from the heart of a patient than the intake valve, when the diaphragm is moved to the blood intake position blood enters the pumping chamber via the intake valve and the outlet valves are in a closed state, when the diaphragm moves to a blood pump position the intake valve closes and blood inside the pumping chamber is forced out through the outlet valves, the pumping chamber is contained within the patient, the gas tube portion contains a non-blood material, a change in the volume of the non-blood material in the gas tube portion shifts the diaphragm between its blood pump position and its blood intake position.

6. The device for pumping blood as claimed in claim 5 further comprising a non-blood pump attached to a proximal end of the gas tube portion for changing the volume of the non-blood material in the gas tube portion.

7. A device for pumping blood comprising an intra-aortic balloon catheter having a balloon membrane and a pumping chamber having a distal end, a larger tube chamber portion, and a communicating smaller tube cannula portion, the larger tube chamber portion has a proximal end, an opening on its proximal end, and a larger outer diameter than the smaller tube cannula portion, the balloon membrane in a deflated state fits within and is passable through the opening on the proximal end of the larger tube chamber portion, the balloon membrane is slidingly disposed within the larger tube chamber portion, the pumping chamber has at least one intake valve adjacent to its distal end and at least one outlet valve closer to the balloon membrane than the intake valve, when the balloon membrane is deflated blood enters the pumping chamber via the intake valve and the outlet valves are in a closed state, when the balloon membrane is inflated the intake valve closes and blood inside the pumping chamber is forced out through the outlet valves, the pumping chamber is for insertion within the patient.

8. The device for pumping blood as claimed in claim 7 wherein the pumping chamber is collapsible.

9. The device for pumping blood as claimed in claim 7 wherein the pumping chamber has the property that when stretched its cross sectional diameter decreases and that when relieved from stretch returns to its previous larger cross sectional diameter.

10. The device for pumping blood as claimed in claim 9 wherein the pumping chamber is made from intercoiled wires.

11. The device for pumping blood as claimed in claim 7 wherein the pumping chamber comprises a stiffening means which holds a stiffening material.

12. The device for pumping blood as claimed in claim 11 wherein the stiffening material is a fluid.

13. The device for pumping blood as claimed in claim 11 wherein the stiffening means comprises a lumen capable of receiving the stiffening material and a supply tube for supplying the stiffening material.

14. The device for pumping blood as claimed in claim 13 wherein the lumen runs in a helical manner around the pumping chamber.

15. A method for inserting a device for pumping blood comprising a pumping chamber having a larger tube chamber portion and a communicating smaller tube cannula portion and an intra-aortic balloon catheter having a balloon membrane and a tip, the smaller tube cannula portion has a distal end, the larger tube chamber portion has a proximal end and an opening on its proximal end, the balloon membrane in a deflated state fits within and is passable through the opening on the proximal end of the larger tube chamber portion, said method comprising the steps of:

a) percutaneously inserting the pumping chamber into a blood vessel of a patient such that the distal end of the pumping chamber is located within a ventricle of the patient; and b) percutaneously inserting the intra-aortic balloon catheter into the blood vessel of the patient such that the tip and balloon membrane pass through the opening in the proximal end of the larger tube chamber portion.

16. A method for inserting a device for pumping blood comprising a collapsible pumping chamber having a larger tube chamber portion and a communicating smaller tube cannula portion and an intra-aortic balloon catheter having a balloon membrane and a tip, and a stiffening means for stiffening the collapsible pumping chamber, the smaller tube cannula portion has a distal end, the larger tube chamber portion has a proximal end and an opening on its proximal end, the balloon membrane in a deflated state fits within and is passable through the opening on the proximal end of the larger tube chamber portion, said method comprising the steps of:

a) percutaneously inserting the pumping chamber in a collapsed state into a blood vessel of a patient such that the distal end of the pumping chamber is located within a ventricle of a patient;

b) stiffening the collapsed pumping chamber; and c) percutaneously inserting the intra-aortic balloon catheter into the blood vessel of the patient such that the tip and balloon membrane pass through the opening in the proximal end of the larger tube chamber portion.

17. A method for inserting a device for pumping blood comprising an intra-aortic balloon catheter having a balloon membrane and a tip, a collapsible pumping chamber having a larger tube chamber portion, a communicating smaller tube cannula portion, a stiffening lumen, and a supply tube, the smaller tube cannula portion has a distal end, the larger tube chamber portion has a proximal end and an opening on its proximal end, the balloon membrane in a deflated state fits within and is passable through the opening on the proximal end of the larger tube chamber portion, comprising the steps of:

a) percutaneously inserting the collapsed pumping chamber into a blood vessel of a patient such that the distal end of the pumping chamber is located within a ventricle of a patient;

b) pumping a stiffening material through the supply tube into the stiffening lumen so as to stiffen the pumping chamber; and c) percutaneously inserting the intra-aortic balloon catheter into the blood vessel of the patient such that the tip and balloon membrane pass through the opening in the proximal end of the larger tube chamber portion.

* * * * *